(12) United States Patent  
Yu et al.

(10) Patent No.: US 8,828,187 B2  
(45) Date of Patent: Sep. 9, 2014

(54) METHOD FOR PROCESSING LIGNOCELLULOSE MATERIAL

(75) Inventors: Xuefeng Yu, Yichang (CN); Zhihong Li, Yichang (CN); Minghua Yu, Yichang (CN); Juan Yao, Yichang (CN); Daiwu Liu, Yichang (CN); Jincheng Lei, Yichang (CN); Zhijun Li, Yichang (CN)

(73) Assignee: Angel Yeast Co., Ltd., Yichang (CN)

( * ) Notice: Subject to any disclaimer, the term of this patent is extended or adjusted under 35 U.S.C. 154(b) by 0 days.

(21) Appl. No.: 13/445,894

(22) Filed: Apr. 12, 2012

(65) Prior Publication Data

US 2012/0193049 A1  Aug. 2, 2012

Related U.S. Application Data

(63) Continuation-in-part of application No. PCT/CN2010/077668, filed on Oct. 12, 2010.

(30) Foreign Application Priority Data

Jan. 6, 2010  (CN) .......................... 2010 1 0003009

(51) Int. Cl.  
*D21C 1/00* (2006.01)  
*C12P 19/14* (2006.01)

(52) U.S. Cl.  
CPC . *C12P 19/14* (2013.01); *Y02E 50/16* (2013.01)  
USPC .......................................................... 162/55

(58) Field of Classification Search  
USPC .......................................................... 162/55  
See application file for complete search history.

(56) References Cited

U.S. PATENT DOCUMENTS 5,899,339 A * 5/1999 Noda ............................ 209/155  
6,495,190 B1 * 12/2002 Yaginuma et al. ............. 426/615  
2010/0055741 A1 * 3/2010 Galvez et al. ................... 435/74

* cited by examiner

*Primary Examiner* — Jacob Thomas Minskey  
(74) *Attorney, Agent, or Firm* — Matthias Scholl P.C.; Matthias Scholl

(57) ABSTRACT

A method for processing a lignocellulose material, comprises the following steps: (1) crushing and sieving the lignocellulose material, and collecting granules with a particle size of between 0.08 and 0.1 mm; (2) mixing the granules obtained in step (1) with water, and dispersing through a colloid mill to yield a suspension with a particle size of 40-80 μm; (3) homogenizing the suspension obtained in the step (2) under high pressure to have a particle size of between 10 and 40 μm; and (4) buffering the suspension obtained in the step (3) with a buffer solution of sodium acetate and acetic-acid, adding cellulase, β-glucosidase, and xylanase, and performing zymolysis for 36-72 hours.

8 Claims, 3 Drawing Sheets

METHOD FOR PROCESSING LIGNOCELLULOSE MATERIAL

CROSS-REFERENCE TO RELATED APPLICATIONS

This application is a continuation-in-part of International Patent Application No. PCT/CN2010/077668 with an international filing date of Oct. 12, 2010, designating the United States, now pending, and further claims priority benefits to Chinese Patent Application No. 201010003009.X filed Jan. 6, 2010. The contents of all of the aforementioned applications, including any intervening amendments thereto, are incorporated herein by reference.

BACKGROUND OF THE INVENTION

1. Field of the Invention

The invention relates to the field of bio-processing, and more particularly to a method for processing lignocellulose material.

2. Description of the Related Art

With the decreasing oil resources, the growing food shortage, and the huge demands of liquid fuels such as ethanol and butanol and other biochemical products such as lactic acid and succinic acid, the use of lignocellulose material for producing fermentable sugar has aroused more and more attention. However, the saccharification of cellulose by an enzyme process requires a special pre-treatment to loosen the structure of crystalline cellulose. The processing method mainly includes an acid method, an alkaline method, a steam explosion method, a wet oxidation method, an organic solvent method, etc.

Methods for separating the shrub stalks into major components by low-intensity steam explosion require a steam explosion device and a steam generator, and the safety requirement of operation is high.

Through a nano-scale crusher, the straws can be crushed to 10-20 µm. The hydrolysis efficiency is improved, and the chemical reagent method can be replaced for processing. However, a lot of energy is consumed during the crushing process, and the temperature of a motor is easy to rise during the dry milling process. The intercooling time is long, and the production efficiency is low.

Methods for extracting lignin with an organic solvent and phosphoric acid require the neutralization and filtering, which is a complex process.

Methods for effectively saccharifying lignocellulose using an alkali liquor need to recover the alkali liquor with an electrodialysis method, in which the cost of power consumption is high.

Methods for acid hydrolysis of lignocellulose through a recirculation reactor require special pretreatment equipment.

Therefore, at present, there is an urgent need to find a processing method with low price and high productivity and involves no environmental pollution, no acid and base, and no high-temperature conditions.

SUMMARY OF THE INVENTION

In view of the above-described problems, it is one objective of the invention to provide a method for processing a lignocellulose material that has a low requirement on equipment and a low processing temperature.

To achieve the above objective, in accordance with one embodiment of the invention, there is provided a method for processing a lignocellulose material, comprises the following steps:

- Step (1): Crushing and sieving the lignocellulose material, and collecting granules with a particle size of 0.08-0.1 mm;
- Step (2): Mixing the granules obtained in the step (1) with water, and dispersing through a colloid mill to yield a suspension with a particle size of 40-80 µm;
- Step (3): Homogenizing the suspension obtained in the step (2) under high pressure to have a particle size of 10-40 µm; and
- Step (4): Buffering the suspension obtained in the step (3) with a buffer solution of sodium acetate and acetic-acid, adding cellulase, β-glucosidase, and xylanase, and performing zymolysis for 36-72 hours.

In the method of the invention, the lignocellulose material is coarsely crushed, then the crushed materials are mixed through a colloid mill, and finally, the plant cell wall is ruptured under high pressure under the action of homogenization, so as to release cellulose. The crystallinity of cellulose is decreased, thereby facilitating the enzymolysis and the improvement of saccharification yield of cellulose.

The homogenization is defined as follows: a premixing material enters a valve area at a low flow speed under high pressure, when the material enters a tiny gap between a controllable valve seat and a valve stem, the flow speed suddenly increases and can reach 300 m/second, and meanwhile, a huge pressure reduction is correspondingly generated. Thus, the strong void effect and vortex action are formed in a small space in extremely short time and hit a homogenizing ring with a high speed to exert the powerful shearing and breaking effects on the material granules. Thus, the original coarse granules in the suspension are processed into super-micro-fine, uniform, and stable liquid-solid phase dispersion.

In a class of this embodiment, the lignocellulose material comprises straws, grass, wood, corn cob, marc, and bagasse.

In a class of this embodiment, in the step (2), a mass ratio between the granules and water is preferably 1:1-5, the dispersing time is 1-2 hours, and the temperature is 70-90° C.

In a class of this embodiment, in the step (3), the pressure of high-pressure homogenization is preferably 50-100 atm, the processing time is 1-2 hours, and the temperature is 60-85° C.

In a class of this embodiment, in the step (4), the addition of cellulase is preferably 10-60 international units per gram of lignocellulose material.

In a class of this embodiment, in the step (4), the addition of β-glucosidase is preferably 40-100 international units per gram of lignocellulose material.

In a class of this embodiment, in the step (4), the addition of xylanase is preferably 60-120 international units per gram of lignocellulose material.

In a class of this embodiment, in the step (4), the pH value of sodium acetate and acetic acid buffer solution is preferably 4.8-5.8.

In a class of this embodiment, in the step (4), the enzymolysis temperature is preferably 40-55° C., and the rotational speed is preferably 80-160 rpm.

In the method of the invention, biomass resources such as maize straws, wheat straws, bagasse, marc, wood chip and other agricultural, industrial and domestic wastes are crushed into granules with different size ranges. Some of the samples with a particle size of 80-100 µm are added to water and dispersed with a colloid mill. The fineness is controlled between 40 µm and 80 µm. Thereafter, the crushed mixture is put into a homogenizer and the cell wall is directly ruptured to release lignin and hemicelluloses. The cellulose crystal grains clad inside are exposed. The grain size is controlled within 10-40 µm, so that cellulase is hydrolyzed directly. The sodium acetate-acetic acid buffer solution sample is added, the pH value is controlled within 4.8-5.5, and then the combined cellulase and xylanase are added for enzymolysis.

The lignocellulose type samples are crushed into granules with different size ranges through a crusher used for crushing the samples. The crushed samples with different size ranges are screened out with a mesh sieve to yield partial samples with a particle size of 80-100 μm after sieving with a 0.08 mm-0.1 mm sieve.

High dispersion of samples is carried out as follows: the samples are mixed with water in certain proportion, and the resulting mixture is pumped to a split colloid mill. The crushed samples are obtained after shearing, grinding, and high-frequency vibration, and the particle size of removed materials is 40-80 μm.

According to the method of the invention, after the lignocellulose materials are dispersed to have a particle size of 10-40 μm, the enzymolysis is carried out under the action of mixed enzymes. The concentration of fermentable sugar in the hydrolysate reaches 148-155 g/L, and the hydrolysis ratio is 95%-98%.

The method of the invention overcomes the defects of complex byproducts, more requirements on equipment, high temperature and high cost in the processing method in the prior art. Not only the cost can be reduced, but also the chemical reagent or high-temperature environment is avoided, the environmental pollution or byproducts are avoided, therefore, the method is a pollution-free and effective processing method and provides a practical and feasible way for the commercial production of fuel ethanol and biochemical products.

DETAILED DESCRIPTION OF THE EMBODIMENTS

Figure 1:
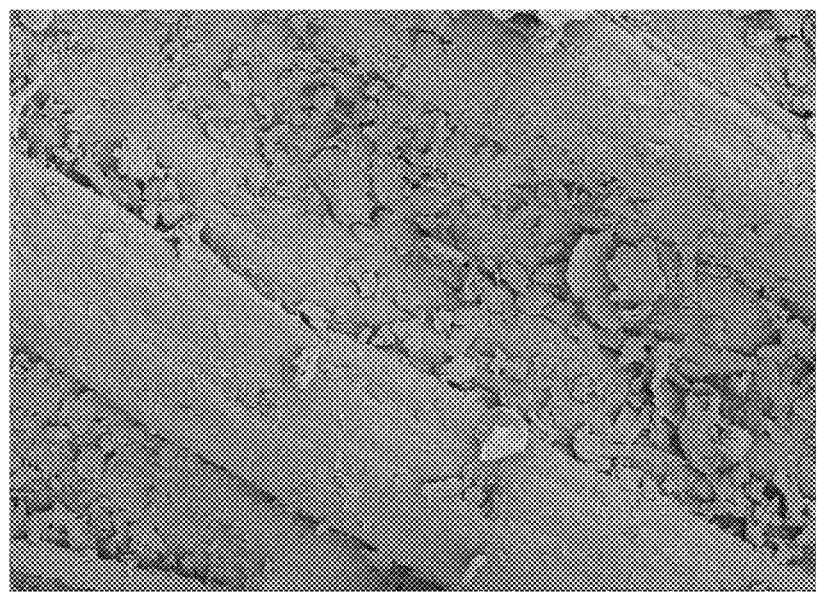
FIG. 1 is a scanning electron micrograph for a straw material before pretreatment.

The following embodiments aim to serve as the further description of the invention.

The detailed description and process are provided for the implementation of the technical scheme of the invention according to the specific implementation, but the scope of protection of the invention is not limited in the following embodiments. The experimental methods without specified conditions in the following embodiments generally follow the normal conditions or conditions suggested by the manufacturer.

The lignocellulose type samples are crushed into granules with different size ranges through a crusher used for crushing the samples. The crushed samples with different size ranges are screened out with a mesh sieve, and then the partial samples with 80-100 μm are obtained after sieving with a 0.08 mm-0.1 mm sieve. The yield is 2 tons per hour, and the power of equipment is 15 kW.

High dispersion of samples is carried out as follows: the samples are mixed with water in certain proportion, and then the mixture is put into a split colloid mill. The crushed samples are obtained after shearing, grinding and high-frequency vibration, and the particle size of removed materials is 40-80 μm. The required maximal size of feeding granules is smaller than 500 microns, the highest feeding temperature is lower than 90° C., the yield is 1 ton per hour, and the power of equipment is 5.5 kW.

High-pressure breaking: the slurry crushed through a colloid mill is pumped to a high-pressure homogenizer. The homogenization is carried out in a homogenizing valve. The non-homogenized premixing material enters the valve area through a reciprocating pump at a low flow speed under high pressure, when the material enters into a tiny gap between a controllable valve seat and a valve stem, the flow speed suddenly increases and can reach 300 m/second, meanwhile, the huge pressure reduction is correspondingly generated, the strong void effect and vortex action are formed in a small space in extremely short time and hit a homogenizing ring with a high speed to exert the powerful shearing and breaking effects on the material granules. Thus, the original more coarse granules in the suspension are processed into supermicro-fine, uniform, and stable liquid-solid phase dispersion. The particle size of removed materials is 10-40 μm, thereby facilitating the saccharification of enzymes. The maximum pressure is 100 atm, the processing capacity is 120 L/hour, and the power of equipment is 3.0 kW.

EXAMPLE 1

Method for Preprocessing Lignocellulose Material

The lignocelluloses materials used herein are maize straws, wheat straws, marc, wood chip, etc. purchased from neighboring areas of Yichang City, Hubei province. The materials are air dried and shaken to remove mud.

1. Coarse Crushing

The straws are crushed with a crusher and sieved with 1 mm, 0.5 mm, 0.1 mm and 0.08 mm sieves, and then the granules with a particle size of 100-800 μm are collected.

2. Rapid Dispersion

Water is added to the straw granules with a particle size of 80-100 μm according to the ratio of 1:1. The mixture is evenly stirred and pumped into a colloid mill, the dispersing time is an hour, the processing temperature is controlled at 70° C., and the evenly dispersed suspension with a particle size of 40-80 μm.

3. High-Pressure Homogenization

The evenly dispersed suspension with a particle size of 40-80 μm is pumped to a high-pressure homogenizer, the homogenization pressure is 50 atm, the processing time is 2 hours, the temperature is controlled at 60° C., and the straw cell wall is broken under high pressure. The suspension with a particle size of 10-40 μm is obtained. After the temperature cools down to 50° C., the corresponding mixed enzymes can be added for enzymolysis.

4. Enzymolysis

The evenly dispersed suspension with a particle size of 10-40 μm is pumped to an enzymolysis reaction kettle, the enzymolysis temperature is 40° C., and the rotational speed is 80 rpm. The cellulase, β-glucosidase, and xylanase are added. The addition of cellulase is 10 international units per gram of lignocellulose material. The addition of β-glucosidase is 40 international units per gram of lignocellulose material, and the addition of xylanase is 60 international units per gram of lignocellulose material. After enzymolysis for 36 hours, the content of sugar in the hydrolysate is determined with a high performance liquid chromatography-evaporative light scattering detection S-method. 150 grams of fermentable sugar is contained in each liter of hydrolysate, and the hydrolysis ratio of cellulose is 95%. The hydrolysis ratio of cellulose is calculated according to the following formula:

Hydrolysis ratio of cellulose=mass of glucose after enzymolysis/(mass of cellulose in the lignocellulose material×1.1)×100%

EXAMPLE 2

Method for Preprocessing Lignocellulose Material

1. Coarse Crushing

The apple pomace is crushed with a crusher and sieved with 1 mm, 0.5 mm, 0.1 mm and 0.08 mm sieves, and then the granules with a particle size of 100-800 μm are collected.

2. Rapid Dispersion

The straw granules with a particle size of 80-100 μm are added with water according to the ratio of 1:5 and evenly stirred, then the mixture is pumped into a colloid mill, the dispersing time is 2 hours, the processing temperature is controlled at 90° C., and the evenly dispersed suspension with a particle size of 40-80 μm.

3. High-Pressure Homogenization

Figure 2:
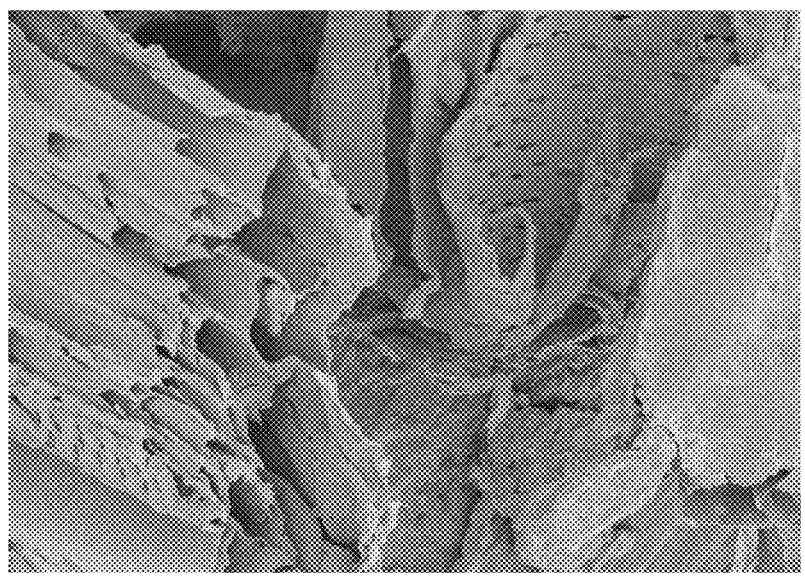
FIG. 2 is a scanning electron micrograph for a straw material after being milled with a colloid mill and dispersed with a homogenizer.

The evenly dispersed suspension with a particle size of 40-80 μm is pumped to a high-pressure homogenizer, the homogenization pressure is 100 atm, the processing time is 1 hour, the temperature is controlled at 85° C., and the high-pressure breaking of the straw cell wall is further realized. The suspension with a particle size of 10-40 μm is obtained. After the temperature reduction, the corresponding mixed enzymes can be added, so as to enter the enzymolysis stage. The granules in the suspension are taken and observed with an electron microscope, as shown in FIG. 2; compared with the scanning electron micrograph for the straw materials before pretreatment in FIG. 1, it can be seen that the void ratio of the straws treated with the method of the invention is increased and the structure of cellulose becomes loose. The structural change is favorable for improving the saccharification rate.

4. Enzymolysis

The evenly dispersed suspension with a particle size of 10-40 μm is pumped to an enzymolysis reaction kettle, the enzymolysis temperature is 55° C., and the rotational speed is 160 rpm. The cellulase, β-glucosidase, and xylanase are added, the addition of cellulase is 60 international units per gram of lignocellulose material, the addition of β-glucosidase is 100 international units per gram of lignocellulose material, and the addition of xylanase is 120 international units per gram of lignocellulose material. After enzymolysis for 72 hours, the content of sugar in the hydrolysate is determined with a high performance liquid chromatography-evaporative light scattering detection S-method, 160 grams of fermentable sugar is contained in each liter of hydrolysate, and the hydrolysis ratio of cellulose is 98%. The hydrolysis ratio of cellulose is calculated according to the following formula:

Hydrolysis ratio of cellulose=mass of glucose after enzymolysis/(mass of cellulose in the lignocellulose material×1.1)×100%

EXAMPLE 3

Comparison Between Method for Preprocessing Lignocellulose Material of the Invention and Other Methods Method 1: Acid Treatment Dilute sulfuric acid with volume fraction of 4%, and lignocellulose material and water with a ratio of 1:3 are put into a reaction kettle. After reaction for 10-30 mins at the temperature of 140-160° C., the mixture is filtered using an air pump, the pH value is adjusted to be neutral to yield a lignocelluloses. The lignocellulose is dried at room temperature and then hydrolyzed with an enzymolysis method. The content of sugar in the hydrolysate is determined with a high performance liquid chromatography-evaporative light scattering detection S-method.

Method 2: Alkaline Treatment

Sodium hydroxide with volume fraction of 1.0%, and lignocellulose material and water with a ratio of 1:3 are put into a reaction kettle. After reaction for 2.5 hours at the temperature of 70-90° C., the mixture is filtered using an air pump, the pH value of is adjusted to be neutral to yield a lignocelluloses. The lignocellulose is dried at room temperature and then hydrolyzed with an enzymolysis method; the content of sugar in the hydrolysate is determined with a high performance liquid chromatography-evaporative light scattering detection S-method.

Method 3: Steam-Explosion Treatment

The lignocellulose material and water are put in an explosive kettle according to the ratio of 1:1. Steam is introduced in the mixture for reaction for 8-15 minutes under the raising pressure of 0.8 MP097382a-1.8 MP097382a. The pneumatic control valve is pressure-released in an instant, and the lignocellulose material enters a receiving vessel through a cyclone separator under the action of pressure difference. The lignocellulose material is cooled to obtain filter residue; the filter residue is dried at room temperature and then hydrolyzed with the enzymolysis method; the content of sugar in the hydrolysate is determined with a high performance liquid chromatography-evaporative light scattering detection S-method.

Figure 3:
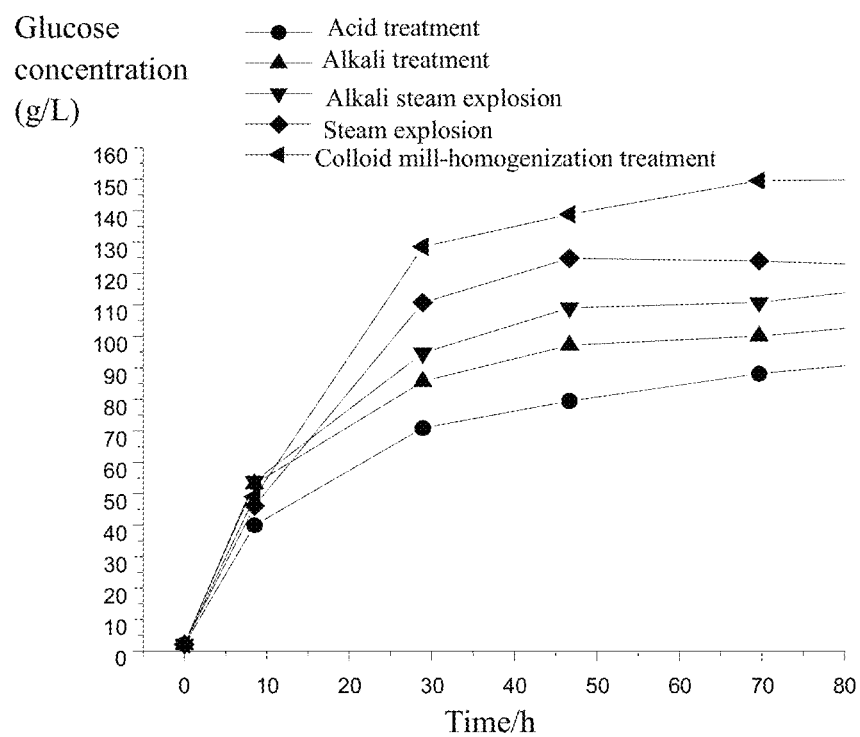
FIG. 3 is a curve of saccharification for a straw material treated with different methods.

The straws treated in the examples 1 and 2 are saccharified as required. FIG. 3 shows the comparison of the saccharification effect of the straws treated using the acid method, alkaline method, and steam explosion method. The results show that the saccharification effect in the method of the invention is better than that in other four processing methods, and the concentration of sugar can reach about 150 g/L.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for saccharification of a lignocellulose material selected from the group consisting of straws, grass, wood, corn cob, marc, and bagasse, the method comprising the following steps:

(1) crushing and sieving the lignocellulose material, and collecting granules with a particle size of 0.08-0.1 mm;

(2) mixing the granules obtained in step (1) with water, and dispersing through a colloid mill to yield a suspension and controlling a particle size of the granules to be 40-80 μm;

(3) homogenizing the suspension obtained in step (2) under a pressure of from 50 to 100 atm in a homogenizer to rupture cell walls of plant cells in the lignocellulose material and to release cellulose from the cell walls, and controlling a particle size of the granules to be 10-40 μm; and (4) buffering the suspension obtained in step (3) with a buffer solution of sodium acetate and acetic-acid, pumping the suspension to an enzymolysis reaction kettle, adding cellulase, β-glucosidase, and xylanase to the suspension, and performing enzymolysis for 36-72 hours in the enzymolysis reaction kettle to obtain a hydrolyzate comprising glucose;

wherein:

a concentration of said glucose is from 148 g/L to 155 g/L of the hydrolyzate; and a hydrolysis ratio of cellulose is from 95 to 98%, and the hydrolysis ratio is calculated by the following equation: hydrolysis ratio of cellulose=mass of glucose in the hydrolyzate/(mass of cellulose in the lignocellulose material×1.1)×100%.

2. The method of claim 1, wherein in step (2), a mass ratio between the granules and the water is 1:1-5, a dispersing time is 1-2 hours, and a temperature is 70-90° C.

3. The method of claim 1, wherein in step (3), said homogenizing is performed for 1-2 hours at a temperature of 60-85° C.

4. The method of claim 1, wherein in step (4), cellulase is present in an amount of 10-60 international units per gram of the lignocellulose material.

5. The method of claim 1, wherein in step (4), β-glucosidase is present in an amount of 40-100 international units per gram of the lignocellulose material.

6. The method of claim 1, wherein in step (4), xylanase is present in an amount of 60-120 international units per gram of the lignocellulose material.

7. The method of claim 1, wherein in step (4), a pH value of the buffer solution of sodium acetate and acetic acid is 4.8-5.8.

8. The method of claim 1, wherein in step (4), said enzymolysis is performed at a temperature of 40-55° C. and at a rotational speed of the enzymolysis reaction kettle of 80-160 rpm.

* * * * *